(12) United States Patent
Vogt et al.

(10) Patent No.: US 8,770,451 B2
(45) Date of Patent: Jul. 8, 2014

(54) CARTRIDGE SYSTEM HAVING A DEVICE FOR SYNCHRONISING TWO FLUID FLOWS

(75) Inventors: Sebastian Vogt, Erfurt (DE); Hubert Buechner, Nuremberg (DE)

(73) Assignee: Heraeus Medical GmbH, Wehrheim (DE)

(*) Notice: Subject to any disclaimer, the term of this patent is extended or adjusted under 35 U.S.C. 154(b) by 0 days.

(21) Appl. No.: 13/822,897

(22) PCT Filed: Aug. 10, 2011

(86) PCT No.: PCT/EP2011/003994
§ 371 (c)(1),
(2), (4) Date: Mar. 13, 2013

(87) PCT Pub. No.: WO2012/038004
PCT Pub. Date: Mar. 29, 2012

(65) Prior Publication Data
US 2013/0181008 A1    Jul. 18, 2013

(30) Foreign Application Priority Data
Sep. 22, 2010  (DE) .......................... 10 2010 046 056

(51) Int. Cl.
*B65D 3/00* (2006.01)

(52) U.S. Cl.
USPC ...................... 222/548; 222/145.5; 222/145.6; 222/137; 222/491

(58) Field of Classification Search
CPC .............. B65D 83/005; B65D 81/325; B05C 17/00553; B29B 7/7438; B29B 7/7657; A61C 5/064
USPC ........ 222/145.5, 145.6, 136, 137, 144, 145.4, 222/387, 494, 485, 502, 503, 545, 547, 548, 222/549; 137/855
See application file for complete search history.

(56) References Cited

U.S. PATENT DOCUMENTS

| 4,260,077 A | 4/1981 | Schroeder |
| 4,432,469 A * | 2/1984 | Eble et al. ...................... 222/134 |

(Continued)

FOREIGN PATENT DOCUMENTS

| DE | 202006015457 U1 | 2/2008 |
| DE | 102007050762 B3 | 5/2009 |
| GB | 2064664 A | 6/1981 |

OTHER PUBLICATIONS

International Search Report for PCT Application No. PCT/EP2011/003994 dated Dec. 21, 2011.

*Primary Examiner* — Frederick C Nicolas
*Assistant Examiner* — Bob Zadeh
(74) *Attorney, Agent, or Firm* — Norris McLaughlin & Marcus, P.A.

(57) ABSTRACT

A cartridge system has two cartridges and a discharge opening, wherein the cartridges are delimited by cartridge walls and by a cartridge head, wherein at least one cartridge opening for expelling the cartridge contents from both cartridges is provided in each case in the cartridge head. A device regulates streams of fluid from the cartridges and is arranged rotatably or slideably on the cartridge head, wherein on at least two openings at least one wing is in each case arranged which at least in some areas protrudes past the opening, such that a flow through the openings applies to the device a force which force leads to a sliding or turning of the device against the cartridge head, such that a housing having a discharge opening is arranged on the cartridge head, in which the housing is arranged so as to rotate or slide.

23 Claims, 4 Drawing Sheets

(56) References Cited

Figure 1:
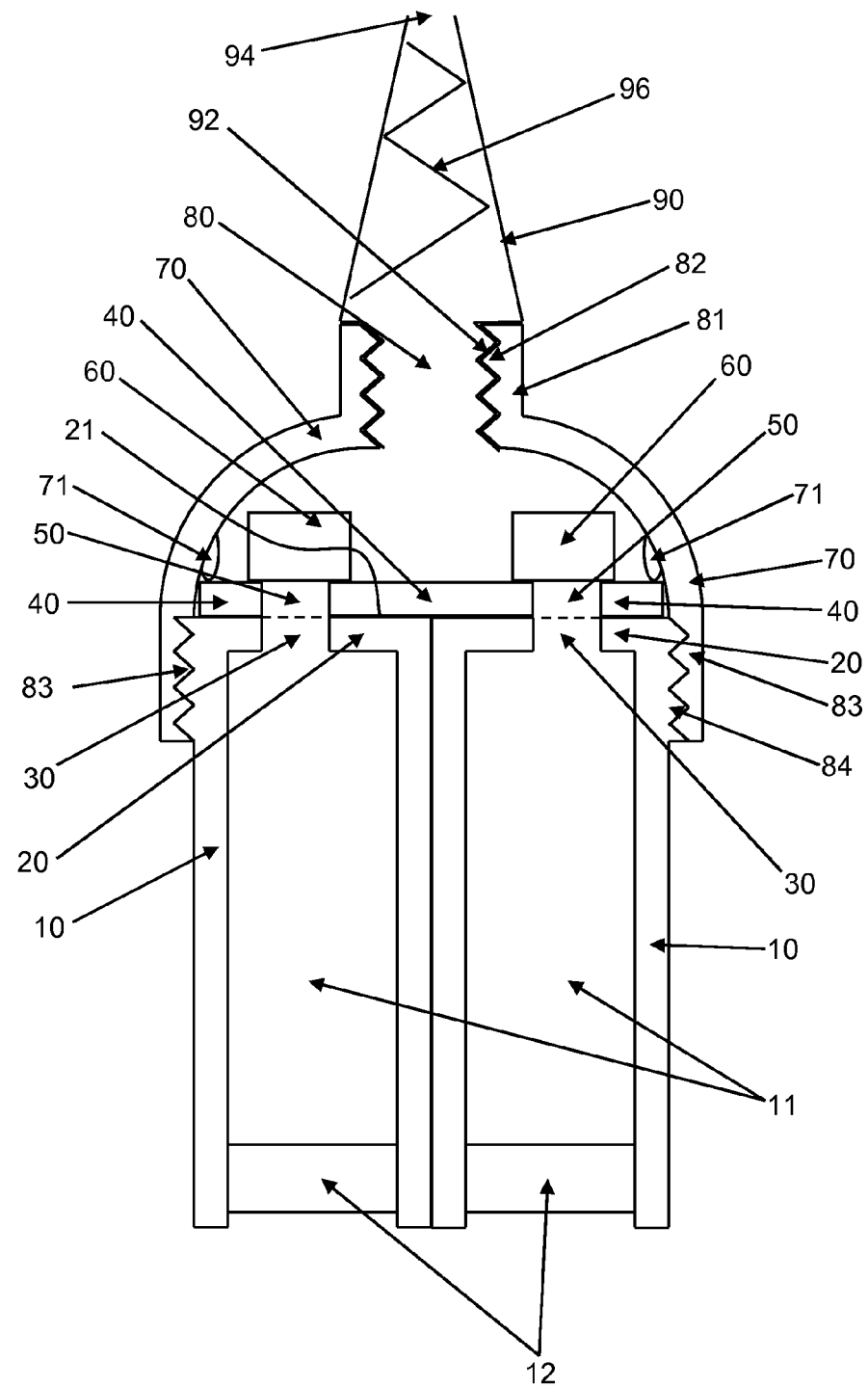

U.S. PATENT DOCUMENTS 5,443,183 A * 8/1995 Jacobsen et al. ........... 222/145.6
6,837,612 B2 * 1/2005 Bublewitz et al. ......... 366/172.1
2004/0257909 A1 12/2004 Pieroni

* cited by examiner

CARTRIDGE SYSTEM HAVING A DEVICE FOR SYNCHRONISING TWO FLUID FLOWS

This is a 371 of PCT/EP2011/003994 filed 10 Aug. 2011 (international filing date), and claims the priority of German Application No. 10 2010 046 056.7 filed 22 Sep. 2010.

The invention relates to a cartridge system for mixing and applying two fluids, in particular of a medical cement, comprising two cartridges and a dispensing opening, whereby the cartridges are bordered through cartridge walls and through a cartridge head, whereby at least one cartridge opening each for expelling the cartridge contents from both cartridges is provided in the cartridge head.

The invention also relates to a device for said cartridge system according to the invention that can be arranged to be rotatable or shiftable on a cartridge head of a cartridge system, a method for synchronising fluid flows using a cartridge system according to the invention or using a device according to the invention for a cartridge system according to the invention, as well as a method for mixing a mixing ware using a cartridge system according to the invention.

Accordingly, a device for synchronising fluid flows is also a subject matter of the invention. The device is intended, in particular, for two-component side-by-side cartridge systems. A method for synchronising fluid flows and the use of the device are also a subject matter of the invention.

An "ideal fluid" is understood, in particular, to mean a substance that poses no resistance to shearing at arbitrarily low velocity. Hereinafter, the term, "fluid", shall encompass mainly incompressible fluids. The term, "fluid flow", shall be understood to mean a moving flowing fluid.

Preferably, the term, "fluid", shall be understood to also mean flowable pastes. A paste is a solid-liquid mixture (suspension) having a high solids content.

Pasty two-component systems are very common in technology and are manufactured in large-scale production for seals and adhesives for use in industry, crafts, and home improvement. Pasty two-component systems are also common in dental technology. Recently, attempts have been made to develop pasty two-component polymethylmethacrylate bone cement systems, such as is known, for example, from DE 10 2007 050 762 B3. Currently, so-called side-by-side cartridges and coaxial cartridges are the customary technology.

All these two-component systems are based on the same basic principle, i.e. an initiator being present in one paste and an accelerator or curing agent being present in the other paste. The pastes are usually stored separately in separate cartridges. The pastes are pushed from said cartridges towards the cartridge head by means of feed plungers arranged therein and the action of pestles. In this context, it is important that the pastes are pressed at the predetermined volume ratio from the cartridges into static mixers which are arranged on each cartridge head. The pastes are mixed in the static mixers and the curing reaction commences. It is essential to the quality of the cured paste material to maintain the mutual volume ratio of the two pastes. Most often the volume ratio of the pastes is in the range of 1:1 to 1:10. The volume ratio is maintained not only through the dimensioning of the cartridges, but also through synchronous propulsion of the feed plungers in the cartridges. Referring to the technical means, said synchronous propulsion is effected by the two feed plungers being connected to each other. In most two components systems, the feed plungers are connected to a toothed rack that is moved towards the cartridge head either through manual force via actuating levers or through motors.

Moreover, it is also feasible to extrude from cartridges using compressed air. In this context, a feed plunger having two pestles on its outside is situated in the cartridge system. During extrusion, compressed air is applied to the feed plunger which is thus made to move towards the cartridge head. The pestles provided on the outside press on the plungers of the cartridges simultaneously. Since both pestles are connected to the feed plunger, they can move to the front towards the cartridge head only in synchronous manner.

It is important to synchronise the dispensing, since the viscosity of the pastes usually is not exactly the same. Accordingly, simply applying pressure from compressed air to non-synchronised plungers would only lead to the feed plunger of the lower viscosity paste being pressed more rapidly towards the cartridge head than the comparably higher viscosity paste. This would change the predetermined volume ratio. This would result in less-than-optimally cured paste material.

Directly applying compressed gas from compressed gas conduits or conventional compressed gas cartridges, such as carbon dioxide cartridges, would be advantageous in that very large forces would act on the feed plungers, which would allow highly viscous pastes to be extruded as well, and in that the extrusion pressure, and thus the extrusion rate, could be controlled by means of simple valves without any need to have mechanical devices such as toothed racks or gears present.

It would be particularly advantageous for applications in the OR to be able to use compressed gas with a cartridge system/an applicator with the smallest possible volume and maximal extrusion force enabling rapid and safe application of pasty two-component polymethylmethacrylate bone cements. For this purpose, it would make sense to have the gas pressure act directly on the feed plungers in the cartridges without any need to have a large-volume synchronisation in the form of feed plungers with pestles.

A generic cartridge system having two cartridges and two feed plungers that are connected to each other is known from U.S. Pat. No. 4,260,077 A. The cartridge system is basically designed like two syringes being positioned right next to each other. A common outlet opening for both cartridge contents is provided on the tip of the cartridge system. Extruding the contents, the feed plungers are pressed into the cartridges until the front ends of the feed plungers touch against the cartridge heads.

In summary, the basic disadvantage of previously known cartridge systems and/or applicator systems for pasty multi-component systems is that the feed plungers and/or pestles that are required for synchronisation of the dispensation of paste and are connected to each other cause the space needs of the applicators to be large since the connected feed plungers need to be at least as long as the cartridges in order to enable near complete dispensation of the pastes from the cartridges by means of moving the feed plungers towards the cartridge head. The feed plungers need to be moved all the way to the cartridge head in order to be able to press all paste contained in the cartridge volume into the static mixer.

Accordingly, it is the object of the invention to develop a method and a device for synchronising and mixing pasty fluids that allow the dispensation of pastes to be synchronised such that pastes differing in viscosity can be pressed from the cartridges into static mixers at a predetermined volume ratio by simply applying compressed gas to the feed plungers in the cartridges. The volume of the cartridge system should be as small as possible. In particular, the length of the synchronisation device should be markedly less than the length of the cartridge.

The object of the invention is met in that a device for regulating fluid flows from the cartridges is arranged on the cartridge head and comprises at least two wings and at least two openings which overlap, at least partly, with at least two cartridge openings, whereby the device is arranged on the cartridge head such as to be rotatable or shiftable, whereby at least two openings have at least one wing each projecting, at least partly, over the opening arranged on them, such that a flow through the openings effects, via the wings, a force that acts on the device and is parallel to the surface of the openings leading to the device being rotated or shifted with respect to the cartridge head upon which the surface area of the cartridge openings overlapping with the device changes, and in that the cartridge head has a housing comprising the dispensing opening arranged on it, in which the device is arranged such as to be rotatable or shiftable.

In the scope of the present invention, wings encompass all surfaces redirecting a fluid flow that transmit a force to the device upon which the same can be rotated or shifted.

In this context, the invention can provide the two cartridges to be cylindrical two-component side-by-side cartridges.

The invention can just as well provide that the device is arranged suitably such that it can be rotated about an axis parallel to the cartridge axis or shifted in a direction perpendicular to the cartridge axis.

Cartridge systems according to the invention can also be characterised in that the cartridge head is provided as a planar surface.

In this context, the invention can provide the device to be a planar, in particular circular, disc having at least two openings and at least two wings arranged on the openings.

The invention can just as well provide the cartridge openings to connect the interior spaces of the cartridges to the upper side of the cartridge head on which the device is arranged.

Cartridge systems according to the invention can be provided to have two cartridge openings in the cartridge head and two openings in the device, whereby the openings overlap with the cartridge openings, at least partly.

It is particularly advantageous for the wings to possess an angle of inclination with respect to the openings of 1° to 89°, preferably 30° to 60°, and particularly preferably 40° to 50°.

The invention can just as well provide the wings to be flat discs, in particular plates.

An embodiment of the invention provides the device to be supported like in a bearing on the cartridge head such as to be shiftable, and the wings to be inclined in opposite directions with respect to the direction of shifting, whereby the forces acting on the wings as a result of a fluid flowing through the openings are directed in opposite directions with respect to the shiftable device.

An alternative embodiment of cartridge system according to the invention provides the device to be supported like in a bearing on the cartridge head such as to be rotatable, and the wings to be inclined in opposite directions with respect to the rotation axis, whereby the torques acting on the wings as a result of a fluid flowing through the openings are directed in opposite directions with respect to the rotation axis of the device.

The invention can also provide the housing to have an internal diameter that is larger than or equal to the device, and the distance from the device to the upper inside of the housing to be larger than the perpendicular line from the outside of the wings to the surface of the device.

Cartridge systems providing the housing to have a guidance for the device on its inside are particularly advantageous.

The invention can provide the dispensing opening to have first attaching means, in particular a thread for a dispensing tube, arranged on it.

Advantageous cartridge systems can just as well provide the cartridges to be bordered on the sides opposite from the cartridge head through one feed plunger each for expelling starting components of the mixing ware from the cartridges, whereby the feed plungers are arranged such as to be mobile in the inside space of the cartridges.

Moreover, the invention can provide a dispensing tube comprising a static mixer to be arranged on the dispensing opening.

Particularly advantageously, the housing has second attaching means, in particular an internal thread, arranged on it that can be used to attach the housing to third attaching means, in particular an external thread, arranged on the cartridges, preferably in detachable manner.

The invention can just as well provide the device to close tightly, in particular fluid-tightly, with respect to the cartridge head such that at least two cartridge openings and at least two openings of the device arranged above them form at least two patent fluid-tight connections from the inside space of the cartridges to the inside space of the housing.

According to a preferred embodiment, the invention can provide that the cartridges can be closed and/or opened through rotating or shifting the device.

The invention also provides a device for a cartridge system of this type that can be arranged on a cartridge head of a cartridge system such as to be rotatable or shiftable, having at least two openings that can be used to overlap at least partially with two cartridge openings of the cartridge system, and at least two wings that are arranged at the edges of the at least two openings and are inclined over the openings.

The object of the invention is also met through a method for synchronising fluid flows using a cartridge system of this type or a device of this type, whereby two fluid flows are pressed through the cartridge openings and through the openings of the device, the fluid flows are redirected by means of the wings, different forces are applied to the wings if the viscosity of the fluids differs due to the difference in flow rate, whereby the device is thus made to rotate or shift, whereby the openings are shifted with respect to the cartridge openings and thus the one passage area that is bordered by one cartridge opening and the opening situated above it is made smaller for the lower viscosity fluid, and the other passage area of the higher viscosity fluid is made larger until the forces acting on the wings become equal due to the change in fluid flows through the passage areas, and the rotary motion or shifting of the device is stopped.

In this context, the invention can provide the fluid flows, once they have been pressed through the openings, to be pressed into the housing and then to be pressed through the dispensing opening out of the housing.

And lastly, the invention also proposes a method for mixing a mixing ware using a cartridge system of this type, in which the cartridge system is used for mixing flowing pasty adhesives, pasty sealants, pasty food items, pasty dental materials, pasty inorganic bone cements and/or pasty polymethylmethacrylate bone cements, in particular through the use of a method of this type.

In this context, the invention can provide the mixed mixing ware to be applied.

The invention is based on the surprising finding that a simple device comprising openings and wings on said openings that are arranged on a cartridge head of two cartridges having at least one cartridge opening each in the cartridge head allows to guide fluid flows through the cartridge openings and openings in the device, which are arranged one above the other, by means of rotating or shifting the device on the cartridge head, in that the rotation or shift leads to a change in the effective area through which the fluids flows flow. In this context, the effective area of the lower viscosity medium is made smaller with respect to the effective area of the higher viscosity medium.

In this context, the effective area of the lower viscosity medium can decrease and/or the effective area of the higher viscosity medium can increase. The change in the effective areas renders the volume flows smaller and/or larger. In other words, the flow resistance of the two fluids is adapted suitably through adapting the effective area of the passage to their viscosity.

The device is propelled, i.e. is rotated or shifted, through the fluid flows impacting on the wings where they are deflected. Said redirection of the fluid flows effects a force that is transmitted from the wings to the device and is proportional to the mass flow, or the momentum of the fluids, as it may be. The device can evade this force through a motion (rotation or shift). With the wings arranged suitably, this leads to a rotation or to a shift of the device which in turn changes the effective size of the opening, which changes the volume flows of the fluids and which changes the forces acting on the wings. The motion ends as soon as a balance is attained between the two forces acting on the wings. Provided the geometry of the cartridge openings is adequate and the geometry and bearing friction of the device, its openings, and wings are adequate, a desired mixing ratio can be attained independent of the viscosity of the fluids to be mixed.

The desired mixing ratio is thus established rapidly. Provided the geometry and frictional losses of the device are adapted appropriately, the cartridge system according to the invention and the methods according to the invention can therefore be used to easily attain an unchanged mixing ratio independent of the viscosity of the two fluids.

Cartridge systems according to the invention can be used for synchronising and mixing flowing pasty adhesives, pasty sealants, pasty food items, pasty dental materials, pasty inorganic bone cements, and pasty polymethylmethacrylate bone cements.

It is also advantageous to provide a set of devices having different wing geometries, openings of different sizes and/or openings of different shapes for a cartridge system according to the invention that can be used to establish different given mixing ratios of two fluids, in particular of medical cements, in two cartridges.

Figure 2:
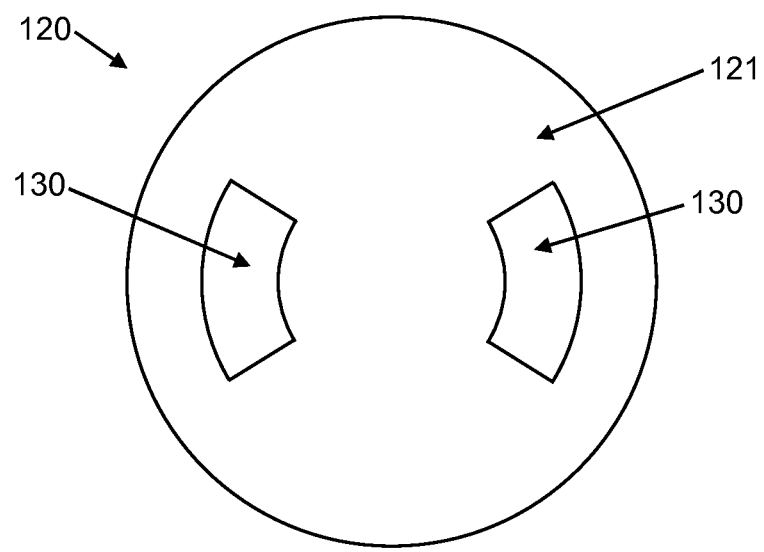
Figure 3:
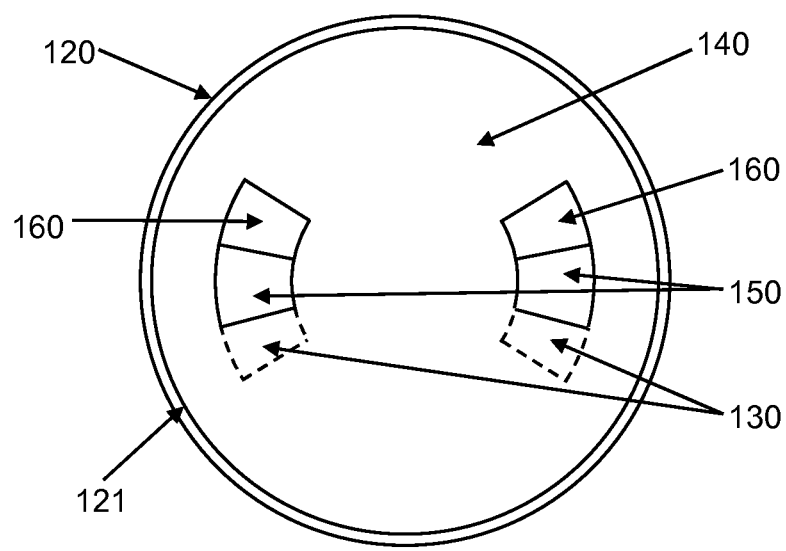
Figure 4:
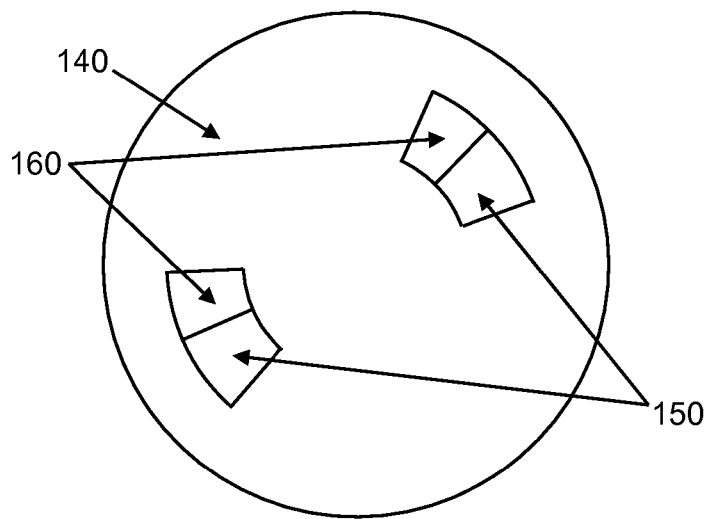
Figure 5:
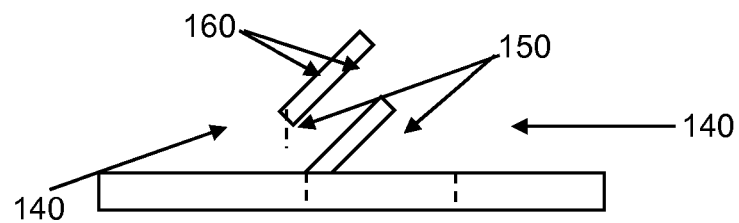
Figure 6:
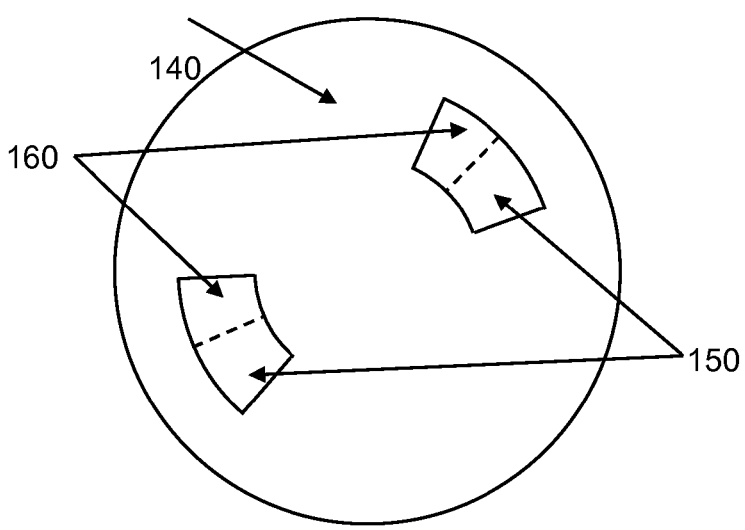
Figure 7:
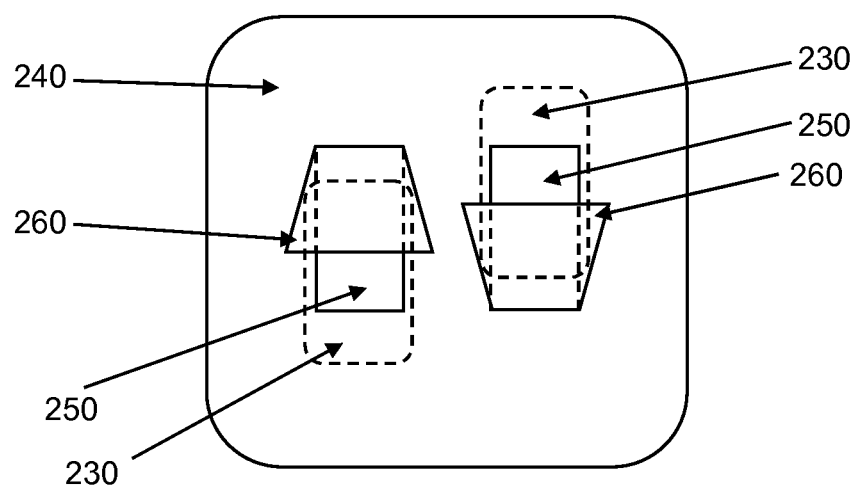
Figure 8:
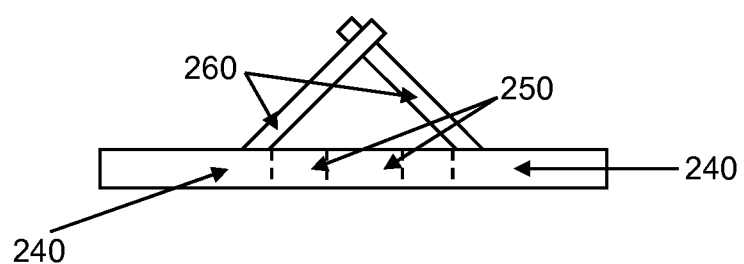

Exemplary embodiments of the invention shall be illustrated in the following on the basis of eight schematic figures, though without limiting the scope of the invention. In the figures:

FIG. 1: shows a schematic cross-sectional view of a cartridge system according to the invention;

FIG. 2: shows a schematic top view onto a cartridge head of a second cartridge system according to the invention;

FIG. 3: shows a schematic top view onto a cartridge head of the cartridge system according to the invention according to FIG. 1 having a rotatable disc;

FIG. 4: shows a schematic top view onto the upper side of a rotatable disc for a cartridge system according to the invention according to FIG. 3;

FIG. 5: shows a schematic side view of the rotatable disc according to FIG. 3;

FIG. 6: shows a schematic top view onto the bottom side of a rotatable disc according to FIG. 3;

FIG. 7: shows a schematic top view onto the upper side of a shiftable device for a third cartridge system according to the invention; and FIG. 8: shows a schematic side view of the rotatable disc according to FIG. 7.

FIG. 1 shows a schematic cross-sectional view of a cartridge system according to the invention. The cartridge system comprises two cylindrical cartridges (10) which each comprise an interior space (11) containing the mixing wares to be mixed (in this case: pastes, in particular medical cements). The cartridges (10) have two cylindrical feed plungers (12) arranged on their floor-side which, together with the interior walls of the cartridges (10), close the interior spaces (11) tightly. The feed plungers (12) are arranged such that they can be shifted in the direction of the cylinder axes of the cartridges (10).

On the side of the cartridges (10) opposite from the feed plungers (12), both cartridges are closed (20) through a cartridge head (20). The cartridge head (20) is bordered on its upper side through a cartridge head external surface (21). Said cartridge head external surface (21) is preferably a planar surface, but can just as well be arced or take any other shape. Two cartridge openings (30) are situated in the cartridge head (20), of which one each opens one of the interior spaces (11) of the cartridges (10) on the head side. Applying a gas pressure (for example compressed air or the gas from a $CO_2$ cartridge) to the floor of the feed plungers (12) propels the feed plungers (12) in the direction of the cartridge head (20). This causes the content of the cartridges (10) to be extruded through the cartridge openings (30).

A device (40) in the form of a disc which also comprises two openings (50) is arranged above the cartridge head (20). The device (40) is supported like in a bearing on the cartridge head (20) such that it can be rotated or shifted and touches with its surface against the cartridge head external surface (21). Accordingly, the cartridge head external surface (21) must be shaped such that it does not prevent or impede the desired motion of the device (40). The two openings (50) partly overlap with the two cartridge openings (30) such as to form two patent effective openings (30, 50). Rotating or shifting the device (40) on the cartridge head (20) changes said surface areas by which the openings (50) overlap with the cartridge openings (30) in such manner that the one effective opening (30, 50) is made larger when the other effective opening (30, 50) is made smaller. Both openings (50) have wings (60) arranged on them that extend obliquely over at least part of the openings. A fluid flowing through the openings (50) impacts on the wings (60) at which it is deflected. This results in a force acting on the device (40) that is a function of the inclination and surface area of the wings (60) and of the mass flows of the fluids from the cartridges (10).

If the two wings (60) are inclined in opposite directions, the device (40) is supported like in a bearing such as to be shiftable in two directions. If the two wings (60) are inclined in the same direction, the device (40) is supported like in a bearing such as to be rotatable. Rotating or shifting causes the openings (50) to shift with respect to the cartridge openings (30) such that the effective opening (30, 50) through which a larger mass flow flows is made smaller, whereas the other effective opening (30, 50) through which the smaller mass flow flows is made larger. A balance will be established once both mass flows become equal for equal wing (60) designs. For different designs, in particular of the surface area of the wings (60), different fluid mixing ratios can be attained in the balanced state.

In any case, the fluids flow exclusively into a space that is covered by means of a cover (70) and in which the fluids mix.

The internal walls of the cover (70) have a guidance (71) arranged on them that keeps the device (40) in position and can limit the mobility of the device (40) in a specific manner. A rotatable bearing of the device (40) can be supported through a centric peg (not shown) on the cartridge head (20) and/or on the device (40) itself. For the device (40) to be shiftable, rails (not shown) or projections (not shown) can be provided on the cartridge head (20), the cover (70) and/or the device (40).

A dispensing opening (80) for the mixed mixing ware, or the mixed fluids, as it may be, is provided on the upper side of the cover (70). The dispensing opening is arranged in a cylindrical connector (81) having a circular footprint. An internal thread (82) is provided on the inside of the connector (81). Attaching means (83), for example snap-in locking means or an internal thread, are arranged on the bottom side of the cover (70). The attaching means (83) can be used to attach the cover (70) to the two cartridges (10). For this purpose, the two cartridges (10) comprise attaching means (84), for example counter snap-in locking means or an external thread, that engage the attaching means (83) of the cover (70).

The purpose of the internal thread (82) of the connector (81) is to attach a dispensing tube (90) comprising an external thread (92) to it. Instead of an internal thread (82) and an external thread (92), the dispensing tube (90) can just as well be attached to the dispensing opening (80) through other attaching means (82, 90). Conceivable for this purpose are, in particular, snap-in means, catches, bayonet closures, adhesive closures, and simple plug-in connections that are easy to assemble, but more complex attaching means, such as flanges, are conceivable as well. The dispensing tube (90) can just as well be fixedly connected to the cover (70), for example as a single part. A dispensing tube tip (94) is arranged on the upper tip of the dispensing tube (90) and can be used to apply the mixing ware. To provide for better mixing of the fluids, a static mixer (96) is arranged in the dispensing tube (90).

The openings for the mixing ware formed in the dispensing tube (90) and the dispensing opening (80) are preferably larger than the two openings (50) taken together and the two cartridge openings (30) taken together. This is to make sure that the largest resistance to the flow of the fluids is generated at the wings (60) of the device (40) and not to reduce the effect thereof through back pressure.

FIG. 2 shows a schematic top view onto a cylindrical cartridge system according to the invention. A cartridge head (120) of the cartridge system is bordered in the direction of the viewer through a cartridge head external surface (121). Two cartridge openings (130) are arranged in the cartridge head (120). Each of the cartridge openings (130) is connected to the inside of a cartridge situated below it (not shown). The two cartridge openings (130) are arranged on a circle of the same radius and are ring segments.

FIG. 3 shows a schematic top view onto the cylindrical cartridge system according to the invention according to FIG. 2, whereby a rotatably supported device (140) for controlling the volume flow through the two cartridge openings (130) is arranged on the cartridge head (120). For this purpose, the device (140), which is provided as a circular disc, comprises two openings (150) parts of which are arranged over the cartridge openings (130) of two cartridges (not visible since they are covered by the cartridge head (120)). Two wings (160) are arranged on the openings (150) in opposite orientations with respect to the rotation axis of the device (140) that is arranged in the centre of the circular disc. The openings (150) and the cartridge openings (130) continue below the wings (160).

FIG. 4 shows the device (140) according to FIG. 3 in a schematic top view. As explained in the context of FIG. 3, the two wings (160) are arranged on the openings (150) in opposite orientations with respect to the rotation axis of the device (140). The openings (150) continue below the wings (160). The straight left upper edges of the two ring segments shown define both the edge of the openings (150) and the beginning of the wings (160). The wings (160) are attached to the device (140) at said straight edges and have opposite straight edges of the wings (160) projecting out of the image plane in the direction of the viewer.

The inclination of the wings (160) is shown better in FIG. 5, which shows a schematic side view of the device (140) shown in FIGS. 3 and 4. The wings (160) are inclined at an angle of 45° with respect to the openings (150) and, in this case, also with respect to the circular disc-shaped planar device (140). A flow of a fluid through the openings (150) from below leads to the fluid flow being partly redirected towards the right by means of the wings (160).

FIG. 6 shows the device (140) shown in FIGS. 3, 4, and 5 in a view from below. The wings (160) can be seen through the openings (150). The dashed edge of the wings (160) is farthest below the device (140) as seen by the viewer and is shown dashed only for this reason, although it is otherwise clearly visible through the openings (150).

The two wings (160) are inclined in opposite directions with respect to the rotary axis of the device (140). This means that, upon the device (140) rotating clockwise in the top view shown in FIG. 3, the right upper wing (160) is inclined in the direction of the rotation, whereas the left lower wing (160) is inclined in the direction of rotation upon a counterclockwise rotation. Different mass flows through the openings (150) being redirected at the wings (160) causes the device (140) to rotate since the torques acting by means of the wings (160) are directed opposite to each other. Accordingly, the scope of the invention includes, for example, a cartridge system for two-component side-by-side cartridges (10) that is characterised in that a) the cartridge head (20, 120) is provided as a planar surface (21, 121) having two cartridge openings (30, 130), whereby the cartridge openings (30, 130) connect the internal space (11) of the cartridges (10) to the upper side of the planar surface (21, 121);

b) a planar disc (40, 140) is arranged on the planar surface (21, 121) of the cartridge head (20, 120);

c) the planar disc (40, 140) contains at least two openings (50, 150) whose surface area is smaller than that of the cartridge openings (30, 130);

d) the disc (40, 140) is arranged such that it can be rotated with respect to the axis of the cartridge system;

e) the disc (40, 140) is arranged such as to be rotatable in such manner that the openings (50, 150) are positioned over the cartridge openings (30, 130);

f) at least two wings (60, 160) that are inclined towards the disc (40, 140) are arranged on the disc (40, 140) at each opening (50, 150), whereby the angle of inclination of the wings (60, 160) with respect to the disc (40, 140) is in the range of 1° to 90°;

g) the wings (60, 160) are arranged adjacent to the openings (50, 150);

h) the wings (60, 160) cover at least a part of the openings (50, 150);

i) the opening angle of the wings (60, 160) points in the same direction;

j) the disc (40, 140) with the openings (50, 150) and the wings (60, 160) is covered through a housing (70), whereby the housing (70) has an internal diameter that is larger than or equal to the disc (40, 140), and whereby the distance from the disc (40, 140) to the upper inside of the housing (70) is larger than the perpendicular line from the outside of the wings (60, 160) to the surface of the disc (40, 140);

k) the housing (70) has a guidance for the disc (40, 140) on its inside;

l) a dispensing opening (80) is arranged on the upper side of the housing (70) and has attaching means (82) for a dispensing tube (90) with a static mixer (96) arranged therein situated on it; and m) attaching means (83) are situated on the bottom side of the housing (70) and can be used to connect the housing (70) to the cartridges (10).

The wings (60, 160) can be implemented simply as obliquely positioned plates (60, 160).

It is particularly advantageous for the cartridge openings (30, 130) to be arranged in the cartridge head (20, 120) in such manner that the openings (50, 150) of the disc (40, 140) with the edge, at which the wings (60, 160) are situated, are in register with one edge each of the cartridge openings (30, 130) when the passage area of both openings (50, 150) that is formed through the overlap of the cross-sections of the cartridge openings (30, 130) and openings (50, 150) for both openings (30, 50, 130, 150) is equal. The cartridge openings (30, 130) have a larger cross-sectional area than the openings (50, 150). The cartridge openings (30, 130) are provided to be larger than the cartridge openings (30, 130) opposite to the edges of the openings (50, 150) at which the wings (60, 160) are arranged are. This means that some part of the cartridge openings (30, 130) is always covered for equal passage areas between the cartridge openings (30, 130) and the openings (50, 150).

The idea underlying the invention is also based on arranging a rotatable disc (40, 140) possessing openings (50, 150) that are at least partly covered through oblique wings (60, 160), whereby the disc (40, 140) is arranged over a planar surface (21, 121) possessing two cartridge openings (30, 130). If fluids differing in viscosity are pressed towards the cartridge head (20, 120), for example through the action of compressed gas on the feed plungers (12), the lower viscosity fluid flows faster than the higher viscosity fluid. When the fluids impact and flow around the oblique wings (60, 160), a force parallel to the disc (40, 140) is applied to the wings (60, 160) perpendicular to the direction of flow. Since the wings (60, 160) are oblique in the same direction, the forces acting on the wings (60, 160) counter-act. If the flow rate of one fluid is lower than that of a second fluid, the force acting on the first wing (60, 160) is smaller than the force acting on the second wing (60, 160) through the fluid having the higher flow rate. Thus, a resultant force acts on the disc (40, 140) and causes a rotary motion of the disc (40, 140). The cartridge openings (30, 130) of the cartridge head (20, 120) are larger than the openings (50, 150) of the disc (40, 140). This causes the faster flowing fluid to rotate the disc (40, 140) in such manner that the opening (50, 150) for the more rapid fluid moves away from the cartridge opening (30, 130) of the cartridges (10) for the more rapid fluid. Thus, the passage area for the fluid decreases and less fluid flows through. Concurrently, the opening (50, 150) of the higher viscosity fluid is rotated along, but in the direction of the cartridge opening (30, 130). Since the cartridge openings (30, 130) are larger than the openings (50, 150), the passage area thus increases. As a result, more fluid can flow through. The rotary motion proceeds until the flow rates of the two fluids are equal and/or the resultant forces are equal and thus balance out. The flow rate of the two fluids is then synchronous.

An advantageous method for synchronising fluids is characterised in that two fluid flows are pushed through the cartridge openings (30, 130) through the planar surface (21, 121). The flows then flow through the openings (50, 150) of the disc (40, 140) and apply a pressure on the wings (60, 160). Subsequently, they enter the housing (70) and exit from the housing (70) through the dispensing opening (80), whereby, for fluids differing in viscosity, the difference in flow rate applies a different force on the wings (60, 160), whereby the forces and/or the torques acting on the wings are directed opposite to each other, and the disc (40, 140) is thus made to rotate. In this context, the openings (50, 150) are shifted with respect to the cartridge openings (30, 130) and thus the passage area of the opening (50, 150) for the lower viscosity fluid is made smaller and the passage area of the higher viscosity fluid is made larger until the forces acting on the wings (60, 160) become equal and thus compensate each other and thus terminate the rotary motion of the disc (40, 140).

FIG. 7 shows a schematic top view onto two cartridge openings (230) and a shiftable device (240) arranged above them for a cartridge system according to the invention, as the one shown, for example, in FIG. 1. FIG. 8 shows a schematic side view of the device (240) according to FIG. 7. The cartridge openings (230) are shown in FIG. 7 as dashed rectangles with rounded corners. Two openings (250) in the shiftable device (240) are provided above the cartridge openings (230) and partly overlap with the cartridge openings (230). In turn, the openings (250) are partly covered by wings (260) that extent obliquely over the openings (250). The covered section of the openings (250) is shown through dashed lines in FIG. 7. The wings (260) form a joint edge with the openings (250). The device (240) is arranged on a cartridge head (not shown) such as to be shiftable such that it can be shifted from top to bottom and vice versa in FIG. 7 and/or can be shifted from left to right and vice versa in FIG. 8.

The wings (260) are inclined in opposite directions with respect to said direction of shifting. Referring to FIG. 7, a larger mass flow through the left cartridge opening (230) and thus through the corresponding opening (250) leads to the mass flow that is deflected downward by means of the left wing (260) being larger than the mass flow that is deflected upward by means of the right wing (260). The device (240) experiences a stronger force due to the left mass flow through the left wing (260) than through the right wing (260) due to the right mass flow. Thus, a resultant force acts on the device (240) and shifts the device (240) upward. The shift makes the overlap of the left opening (250) and the left cartridge opening (230) smaller. This reduces the volume flow and thus the mass flow from the left cartridge (not shown) through the left cartridge opening (230) and the left opening (250). Concurrently, the surface area, in which the right opening (250) overlaps with the right cartridge opening (230) gets larger. This increases the volume flow and thus the mass flow from the right cartridge (not shown) that is arranged below the right cartridge opening (230).

As soon as the mass flows are equal (the volume flows are equal when the masses of the fluids are equal), the two forces acting on the wings (260) are equal and the position of the device (240) is not changed any more. This allows a desired mixing ratio to be attained with a shiftable device (240) as well. The device (240) shown in FIGS. 7 and 8 will produce a mixing ratio of approximately 1:1 if the densities of the liquids are approximately equal. Changing the geometry of the wings (260) and the sizes of the openings (250) and cartridge openings (230) allows basically any mixing ratios to be attained.

The difference between the rotatable devices (for example (140)) and the shiftable devices (for example (240)) according to the scope of the invention is that opposite torques are generated through the fluid flows in the case of rotatable devices, whereas opposite forces are generated through the fluid flows from the two cartridges in the case of shiftable devices.

The features of the invention disclosed in the preceding description and in the claims, figures, and exemplary embodiments, can be essential for the implementation of the various embodiments of the invention both alone and in any combination.

LIST OF REFERENCE NUMBERS

10 Cartridge
11 Internal space
12 Feed plunger
20, 120 Cartridge head
21, 121 Cartridge head external surface
30, 130, 230 Cartridge opening
40, 140, 240 Device/disc
50, 150, 250 Opening
60, 160, 260 Wing/plate
70 Housing
71 Guidance
80 Dispensing opening
81 Connector
82, 83 Fastening means/internal thread
84 Fastening means/external thread
90 Dispensing tube
92 Fastening means/external thread
94 Dispensing tube tip
96 Static mixer

The invention claimed is:

1. A cartridge system, for mixing and applying two fluids or flowable pastes, comprising two cartridges (10) and a dispensing opening (80), whereby the two cartridges (10) are bordered through cartridge walls and through a cartridge head (20, 120), whereby at least one cartridge opening (30, 130, 230), each for expelling the cartridge contents from both cartridges (10), is provided in the cartridge head, wherein a device (40, 140, 240), for regulating fluid flows from the cartridges (10), is arranged on the cartridge head (20, 120) and comprises at least two wings (60, 160, 260) and at least two openings (50, 150, 250) which overlap, at least partly, with at least two cartridge openings (30, 130, 230), whereby the device (40, 140, 240) is arranged on the cartridge head (20, 120) to be rotatable or shiftable, whereby the at least two openings (50, 150, 250) have arranged thereon at least one wing (60, 160, 260) each projecting, at least partly, over the openings (50, 150, 250), such that a fluid flow through the at least two openings (50, 150, 250) effects, via the wings (60, 160, 260), a force as a result of the fluid flow that acts on the device (40, 140, 240) and is parallel to an axis of the at least two openings (50, 150, 250) leading to the device (40, 140, 240) being rotated or shifted with respect to the cartridge head (20, 120) upon which surface area of the cartridge openings (30, 130, 230) overlapping with the device (40, 140, 240) changes, and in that the cartridge head (20, 120) has a housing (70) comprising the dispensing opening (80) arranged on the cartridge head, in which the device (40, 140, 240) is arranged to be rotatable or shiftable.

2. The cartridge system according to claim 1, wherein the two cartridges (10) are cylindrical two-component side-by-side cartridges (10).

3. The cartridge system according to claim 2, wherein the device (40, 140, 240) is arranged suitably such that the device is rotatable about an axis parallel to the cartridge axis or shifted in a direction perpendicular to the cartridge axis.

4. The cartridge system according to claim 1, wherein the cartridge head (20, 120) is provided as a planar surface (121).

5. The cartridge system according to claim 4, wherein the device (40, 140, 240) is a planar circular disc (140, 240) having the at least two openings (50, 150, 250) and the at least two wings (60, 160, 260) arranged on the at least two openings.

6. The cartridge system according to claim 1, wherein the cartridge openings (30, 130, 230) connect the interior spaces (11) of the two cartridges (10) to an upper side of the cartridge head (20, 120) on which the device (40, 140, 240) is arranged.

7. The cartridge system according to claim 1, wherein the cartridge openings (30, 130, 230) are provided in the cartridge head whereby the at least two openings (50, 150, 250) overlap with the cartridge openings (30, 130, 230), at least partly.

8. The cartridge system according to claim 1, wherein the wings (60, 160, 260) comprise an angle of inclination with respect to the at least two openings (50, 150, 250) of 1° to 89°.

9. The cartridge system according to claim 1, wherein the wings (60, 160, 260) are flat discs.

10. The cartridge system according to claim 1, wherein the device (40, 240) is supported on the cartridge head (20) to be shiftable, and the wings (60, 260) are inclined in opposite directions with respect to the direction of shifting, whereby forces acting on the wings (60, 260) as a result of a fluid flowing through the at least two openings (50, 250) are directed in opposite directions with respect to the shiftable device (40, 240).

11. The cartridge system according to claim 1, wherein the device (40, 140) is supported on the cartridge head (20, 120) to be rotatable, and the wings (60, 160) are inclined in opposite directions with respect to the rotation axis, whereby torques acting on the wings (60, 160) as a result of a fluid flowing through the openings (50, 150) are directed in opposite directions with respect to the rotation axis of the device (40, 140).

12. The cartridge system according to claim 1, wherein the housing (70) has an internal diameter that is larger than or equal to the device (40, 140, 240), and a distance of the device (40, 140, 240) from an upper inside of the housing (70) is larger than a perpendicular line from an outside of the wings (60, 160, 260) to a surface of the device (40, 140, 240).

13. The cartridge system according to claim 1, wherein the housing (70) has a guidance (71) for the device (40, 140, 240) on an inside of the housing.

14. The cartridge system according to claim 1, wherein the dispensing opening (80) has first attaching means (82) arranged on the dispensing opening.

15. The cartridge system according to claim 1, wherein the cartridges (10) are bordered on the sides opposite from the cartridge head (20, 120) through one feed plunger (12) each for expelling starting components of a mixture from the cartridges (10), whereby the feed plungers (12) are arranged to be mobile in the inside space (11) of the cartridges (10).

16. The cartridge system according to claim 1, further comprising: a dispensing tube (90), comprising a static mixer (96), arranged on the dispensing opening (80).

17. The cartridge system according to claim 1, wherein the housing (70) has second attaching means (83) arranged on the housing that is usable to attach the housing (70) to third attaching means (84) arranged on the cartridges (10).

18. The cartridge system according to claim 1, wherein the device (40, 140, 240) closes fluid-tightly with respect to the cartridge head (20, 120) such that at least two cartridge openings (30, 130, 230) and the at least two openings (50, 150, 250) of the device (40, 140, 240) arranged above form at least two fluid-tight connections from an inside space (11) of the cartridges (10) to an inside space of the housing (70).

19. The cartridge system according to claim 1, wherein the cartridges (10) are closed or opened through rotating or shifting the device (40, 140, 240).

20. A device (40, 140, 240) for the cartridge system according to claim 1 that is arrangeable on a cartridge head (20, 120) of the cartridge system to be rotatable or shiftable, the device comprises the at least two openings (50, 150, 250) usable to cover the at least two cartridge openings (30, 130, 230) of the cartridge system, and the at least two wings (60, 160, 260) arranged at edges of the at least two openings (50, 150, 250) and inclined over at least a portion of the at least two openings (50, 150, 250).

21. A method for synchronising fluid flows using the cartridge system according to claim 1, comprising
    pressing two fluid flows through the cartridge openings (30, 130, 230) and through the at least two openings (50, 150, 250) of the device (40, 140, 240);
    redirecting the fluid flows by means of the wings (60, 160, 260);
    applying different forces to the wings (60, 160, 260) if the viscosity of the fluids differs due to the difference in flow rate; wherein the device (40, 140, 240) is rotatable or shiftable, whereby the at least two openings (50, 150, 250) are shiftable with respect to the cartridge openings (30, 130, 230) and thus a first passage area that is bordered by one cartridge opening (30, 130, 230) and the at least two openings (50, 150, 250) situated above the first passage area is made smaller for the lower viscosity fluid, and a second passage area for a higher viscosity fluid is made larger until forces acting on the wings (60, 160, 260) become equal due to the change in fluid flows through the first and second passage areas, and the rotary motion or shifting of the device (40, 140, 240) is stopped.

22. The method according to claim 21, wherein the fluid flows, once pressed through the openings (50, 150, 250), are pressed into the housing (70) and are then pressed through the dispensing opening (80) out of the housing (70).

23. A method, for mixing two fluids or flowable pastes, comprising:
    mixing the two fluids or flowable pastes with the cartridge system according to claim 1 to form a mixture, wherein the mixture is a flowing pasty adhesive, a pasty sealant, a pasty food item, a pasty dental material, a pasty inorganic bone cement or a pasty polymethylmethacrylate bone cement.

* * * * *